(12) United States Patent
Wold et al.

(10) Patent No.: US 8,353,426 B2
(45) Date of Patent: Jan. 15, 2013

(54) GAS GENERATION DISPENSER METHOD FOR ON-DEMAND FLUID DELIVERY

(75) Inventors: Truman Wold, Paauilo, HI (US); John Howard Gordon, Salt Lake City, UT (US); Ashok V. Joshi, Salt Lake City, UT (US)

(73) Assignee: Microlin, LLC., Salt Lake City, UT (US)

( * ) Notice: Subject to any disclaimer, the term of this patent is extended or adjusted under 35 U.S.C. 154(b) by 0 days.

(21) Appl. No.: 13/323,332

(22) Filed: Dec. 12, 2011

(65) Prior Publication Data
US 2012/0145742 A1 Jun. 14, 2012

Related U.S. Application Data

(62) Division of application No. 11/923,490, filed on Oct. 24, 2007, now Pat. No. 8,113,390.

(60) Provisional application No. 60/912,463, filed on Apr. 18, 2007.

(51) Int. Cl.
*G01F 11/00* (2006.01)
(52) U.S. Cl. .............................. 222/1; 222/389
(58) Field of Classification Search .............. 222/387, 222/389, 129, 397, 399, 1
See application file for complete search history.

(56) References Cited

U.S. PATENT DOCUMENTS

| | | |
|---|---|---|
| 446,953 A | 2/1891 | Robert |
| 575,365 A | 1/1897 | Mayer et al. |
| 806,844 A | 12/1905 | Rosenstock |
| 957,449 A | 5/1910 | Walz |
| 1,099,720 A | 6/1914 | Peck |
| 1,222,756 A | 4/1917 | Griner |
| 1,921,821 A | 8/1933 | Higgins |
| 2,219,959 A | 10/1940 | Laidley |
| 2,236,525 A | 4/1941 | Davis et al. |
| 2,481,296 A | 9/1949 | Dupuy |
| 2,670,236 A | 2/1954 | Bradburn |
| 2,710,164 A | 6/1955 | Hare |
| 2,740,662 A | 4/1956 | Scott |
| 2,801,879 A | 8/1957 | Dick |
| 2,867,360 A | 1/1959 | Sharma |
| 2,991,517 A | 7/1961 | Bundy |
| 3,127,786 A | 4/1964 | Wooley |

(Continued)

FOREIGN PATENT DOCUMENTS

FR 2082589 12/1971

(Continued)

OTHER PUBLICATIONS

Hwu, Davis D., "PCT International Search Report for PCT/US05/23523", (Dec. 4, 2006),1-3.

(Continued)

*Primary Examiner* — Kevin P Shaver
*Assistant Examiner* — Daniel R Shearer
(74) *Attorney, Agent, or Firm* — David Fonda (57) ABSTRACT

A method of dispensing a fluid comprising generating a gas from a liquid, directing the gas to an expandable gas chamber to expand a volume of the expandable gas chamber, reducing a volume of a fluid chamber in response to expansion of the expandable gas chamber to dispense an amount of the fluid from the fluid chamber, and removing the gas from the expandable gas chamber to collapse the expandable gas chamber.

7 Claims, 9 Drawing Sheets

U.S. PATENT DOCUMENTS

| | | | |
|---|---|---|---|
| 3,169,705 A | 2/1965 | Geiger | |
| 3,254,841 A | 6/1966 | Loncker | |
| 3,482,929 A | 12/1969 | Gentil | |
| 3,685,734 A | 8/1972 | Paciorek et al. | |
| 3,804,592 A | 4/1974 | Garbe et al. | |
| 3,955,930 A | 5/1976 | Shapiro | |
| 4,017,030 A | 4/1977 | Coplan et al. | |
| 4,158,440 A | 6/1979 | Sullivan et al. | |
| 4,166,478 A | 9/1979 | Sugimura et al. | |
| 4,169,757 A | 10/1979 | Kirjavainen | |
| 4,265,373 A | 5/1981 | Stoody | |
| 4,294,778 A | 10/1981 | Deluca | |
| 4,312,347 A | 1/1982 | Magoon et al. | |
| 4,328,843 A | 5/1982 | Fujii | |
| 4,339,079 A | 7/1982 | Sato et al. | |
| 4,399,942 A | 8/1983 | Chand | |
| 4,408,635 A | 10/1983 | Packer | |
| 4,427,030 A | 1/1984 | Jouwsma | |
| 4,468,220 A | 8/1984 | Willbanks | |
| 4,477,414 A | 10/1984 | Muramoto et al. | |
| 4,522,698 A * | 6/1985 | Maget | 204/265 |
| 4,526,320 A | 7/1985 | von Philipp et al. | |
| 4,574,494 A | 3/1986 | Mailliet et al. | |
| 4,621,768 A | 11/1986 | Lhoste et al. | |
| 4,632,310 A | 12/1986 | Konicek | |
| 4,697,549 A | 10/1987 | Hair | |
| 4,753,389 A | 6/1988 | Davis | |
| 4,809,912 A | 3/1989 | Santini | |
| 4,846,003 A | 7/1989 | Marquiss | |
| 4,871,544 A | 10/1989 | Eckenhoff | |
| 4,886,514 A | 12/1989 | Maget | |
| 4,917,301 A | 4/1990 | Munteanu | |
| 4,948,047 A | 8/1990 | Zembrodt | |
| 4,966,767 A | 10/1990 | Eckenhoff | |
| 4,969,874 A | 11/1990 | Michel et al. | |
| 4,995,555 A | 2/1991 | Woodruff | |
| 5,074,252 A | 12/1991 | Morgan, Jr. | |
| 5,143,259 A | 9/1992 | Williams | |
| 5,196,002 A | 3/1993 | Hanover et al. | |
| 5,357,793 A | 10/1994 | Jouwsma | |
| 5,368,863 A | 11/1994 | Eckenhoff et al. | |
| 5,398,851 A | 3/1995 | Sancoff et al. | |
| 5,427,870 A | 6/1995 | Joshi et al. | |
| 5,437,410 A | 8/1995 | Babasade | |
| 5,454,922 A | 10/1995 | Joshi et al. | |
| 5,462,741 A | 10/1995 | Carr et al. | |
| 5,474,785 A | 12/1995 | Wright et al. | |
| 5,538,605 A | 7/1996 | Joshi et al. | |
| 5,549,037 A | 8/1996 | Stumphauzer et al. | |
| 5,567,287 A | 10/1996 | Joshi et al. | |
| 5,591,395 A | 1/1997 | Schroeder et al. | |
| 5,638,868 A | 6/1997 | Loran | |
| 5,647,515 A * | 7/1997 | Zwijnenberg et al. | 222/389 |
| 5,681,435 A | 10/1997 | Joshi et al. | |
| 5,700,245 A | 12/1997 | Sancoff et al. | |
| 5,707,499 A | 1/1998 | Joshi et al. | |
| 5,714,160 A | 2/1998 | Magruder et al. | |
| 5,744,014 A | 4/1998 | Gordon et al. | |
| 5,765,751 A | 6/1998 | Joshi | |
| 5,785,688 A | 7/1998 | Joshi et al. | |
| 5,810,253 A | 9/1998 | Ohayon | |
| 5,855,761 A | 1/1999 | Joshi | |
| 5,871,125 A | 2/1999 | Gross | |
| 5,899,381 A | 5/1999 | Gordon et al. | |
| 5,915,925 A | 6/1999 | North, Jr. | |
| 5,921,251 A | 7/1999 | Joshi | |
| 5,932,204 A | 8/1999 | Joshi | |
| 5,951,538 A * | 9/1999 | Joshi et al. | 604/500 |
| 5,954,268 A | 9/1999 | Joshi et al. | |
| 5,971,713 A | 10/1999 | North, Jr. | |
| 5,997,821 A | 12/1999 | Joshi | |
| 6,042,704 A | 3/2000 | Joshi et al. | |
| 6,045,055 A | 4/2000 | Joshi et al. | |
| 6,060,196 A | 5/2000 | Gordon et al. | |
| 6,082,117 A | 7/2000 | Funatsu et al. | |
| 6,109,539 A | 8/2000 | Joshi et al. | |
| 6,135,126 A | 10/2000 | Joshi | |
| 6,220,267 B1 | 4/2001 | Joshi | |
| 6,283,461 B1 | 9/2001 | Joshi et al. | |
| 6,289,241 B1 | 9/2001 | Phipps | |
| 6,378,780 B1 | 4/2002 | Martens, III et al. | |
| 6,415,808 B2 | 7/2002 | Joshi | |
| 6,527,012 B1 | 3/2003 | Weber | |
| 6,553,712 B1 | 4/2003 | Majerowski et al. | |
| 6,622,755 B2 | 9/2003 | Weber | |
| 6,715,300 B2 | 4/2004 | Longsworth | |
| 6,787,008 B2 | 9/2004 | Joshi et al. | |
| 6,805,306 B1 | 10/2004 | Huang | |
| 6,813,944 B2 | 11/2004 | Mayer et al. | |
| 6,901,965 B2 | 6/2005 | Baltes et al. | |
| 7,048,009 B2 | 5/2006 | Verhaeghe | |
| 7,149,417 B2 | 12/2006 | Joshi et al. | |
| 976,992 A1 | 10/2010 | Effantin et al. | |
| 2002/0158156 A1 | 10/2002 | Joshi et al. | |
| 2002/0175191 A1 | 11/2002 | Joshi et al. | |
| 2004/0135005 A1 | 7/2004 | Duquet | |
| 2005/0023371 A1 | 2/2005 | Joshi et al. | |
| 2005/0150449 A1 | 7/2005 | Matsunaga et al. | |
| 2005/0218074 A1 | 10/2005 | Pollock | |
| 2005/0279776 A1 | 12/2005 | Decottignies et al. | |
| 2007/0001024 A1 | 1/2007 | Wold et al. | |

FOREIGN PATENT DOCUMENTS

| | | |
|---|---|---|
| GB | 191400142 | 0/1914 |
| JP | 00374/140 | 1/1940 |
| JP | 4221275 | 12/1967 |
| JP | 155896/1978 | 5/1980 |
| JP | 91380/1983 | 9/1983 |
| JP | 305870/1988 | 12/1988 |
| JP | 181871/1989 | 7/1989 |
| JP | 64648/1991 | 6/1991 |
| JP | 70141/1991 | 7/1991 |
| JP | 00156/1993 | 1/1993 |
| JP | 317401/1993 | 12/1993 |
| JP | 155367/1995 | 6/1995 |
| JP | 182783/1997 | 7/1997 |
| JP | 276387/1997 | 10/1997 |
| JP | 47253/1999 | 2/1999 |
| JP | 0724201 | 8/2008 |
| WO | WO-00/76645 | 12/2000 |
| WO | WO-2004/020005 | 3/2004 |

OTHER PUBLICATIONS

Hwu, Davis D., "PCT Written Opinion of the International Searching Authority for PCT/US05/23523", (Dec. 4, 2006),1-3.

Nguyen, Dinh Q., "PCT International Search Report for PCT/US05/21022", (May 10, 2007),1-3.

Nguyen, Dinh Q., "PCT Written Opinion of the International Searching Authority for PCT/US05/21022", (May 10, 2007),1-3.

Nguyen, Dinh Q., "Office Action Summary for U.S. Appl. No. 10/868,203", (Aug. 14, 2007),1-5.

Kim, Christopher S., "Office Action for U.S. Appl. No. 09/649,563 sent Sep. 10, 2003",1-5.

Kim, Christopher S., "Office Action for U.S. Appl. No. 09/649,563 send Apr. 13, 2004",1-6.

Kim, Christopher S., "Office Action for U.S. Appl. No. 09/649,563 sent Aug. 25, 2006",1-6.

Kim, Christophe S., "Office Action for U.S. Appl. No. 09/649,563 sent Jun. 12, 2007",1-7.

Nguyen, Dinh "Office Action for U.S. Appl. No. 11/160,642 sent May 1, 2008",1-7.

Kim, "Office Action for U.S. Appl. No. 09/649,563 sent Feb. 15, 2008",1-9.

Nguyen, Dinh "Office Action for U.S. Appl. No. 10/868,203 sent Mar. 17, 2008",1-7.

Varga, Viktoria "European Search Report for EP05790118.3 sent Nov. 7, 2007",1-3.

Josh, et al., "Application for U.S. Appl. No. 09/649,563, filed Aug. 28, 2000",1-33.

Kim, "Office Action for U.S. Appl. No. 09/649,563 sent Jul. 9, 2008",1-8.

Varga, Viktoria "Communication pursuant to Article 94(3) EPC", (Aug. 20, 2008),1-6.

Kim, "Office Action for U.S. Appl. No. 09/649,563 sent Dec. 30, 2008",1-8.
Nguyen, Dinh "Office Action for U.S. Appl. No. 10/868,203 sent Dec. 15, 2008",1-6.
Nguyen, Dinh "Office Action for U.S. Appl. No. 11/160,642 sent Dec. 10, 2008",1-8.
Kang, Sang Yoon "Written Opinion of the International Searching Authority", International App. No. PCT/US2008/080988, (Jul. 2, 2009),1-4.
Kang, Sang Yoon "International Search Report", International App. No. PCT/US2008/080988, (Jul. 2, 2009),1-3.
Shelborne, K "Non-Final Office Action", U.S. Appl. No. 08/880,124 (Apr. 13, 1998),1-6.
Shelborne, K "Non-Final Office Action", U.S. Appl. No. 08/880,124 (Oct. 6, 1998),1-3.
Guillem, Gisbert I., "European Search Report", EP app. No. 98930214.6.(corresponding to U.S. Appl. No. 08/880,124, (Dec. 28, 2009),1-3.
Guillem, Gisbert I., "Communication Pursuant to Article 94(3) EPC (European Office Action)", EP App No. 98930214.6 (corresponding to U.S. Appl. No. 08/880,124, (Oct. 15, 2010),1-6.
Kokubo, Katsui "Notice of Reason for Rejection", JP App. No. 11-504624 (Corresponding to U.S. Appl. No. 08/880,124, (Jul. 29, 2008),1-5.
Nakazawa, Noboru "Notice of Reason for Rejection", JP App. No. 11-504624 (Corresponding to U.S. Appl. No. 08/880,124, (May 19, 2009),1-6.
Unknown, "English Translation of Utility Model Publication JP 42-21275", Translation of JP 42-21275 (supplied by Japanese patent office), (Dec. 7, 1967),1-4.
Kawamura, Norio "English Abstract of JP 07-24201", English Abstract of JP 07-24201, (Aug. 21, 2008),1-2.
Lawrence, Dorithia "International Search Report", PCT US 98/12379 (corresponding to U.S. Appl. No. 08/880,124, (Sep. 30, 1998),1.
Shelborne, Kathryne E., "International Preliminary Examination Report", PCT US 98/12379 (corresponding to U.S. Appl. No. 08/880,124, (Feb. 11, 1999),1-4.
Weldon, K "Non-Final Office Action", U.S. Appl. No. 99/028,372, (Jun. 22, 1999),1-7.
Weldon, K "Final Office Action", U.S. Appl. No. 99/028,372, (Nov. 15, 1999),1-7.
Moeremans, Benoit "Communication Pursuant to Article 94(3) EPC", EP App. No. 99925948.4, (Sep. 12, 2011),1-5.
Honma, T "Official Notice of Reason of Preliminary Rejection (Japan)", JP App. No. 621054/2000 (Corresponding to U.S. Appl. No. 09/028,372, (Mar. 23, 2004),1-4.
Honma, T "Official Notice of Reason of Preliminary Rejection", JP App. No. 621054/2000 (Corresponding to U.S. Appl. No. 09/028,372, (Jun. 14, 2005),1-3.
Unknown Japanese Patent Examiner, "Official Notice of Reason for Final Rejection", JP App. No. 621054/2000 (Corresponding to U.S. Appl. No. 09/028,372, (May 30, 2006),1.
Inoue, Perfume "English Abstract", JP App. No. 64648/1991, (Jun. 24, 1991),1.
Rifure Co., "English Abstract (Abridged)", JP App. No. 70141/1991, (Jul. 12, 1991),1.
Sakomoto, Susumu "English Abstract", JP patent No. 1181871, (Jul. 19, 1989),1.
Yamamori, Seiji "English Abstract", JP Patent App. No. 5000156 (JP Opened Patent App. No. 00156/1993), (Jan. 8, 1993),1.
Kubo, Tsugio "English Abstract", JP Patent App. No. 317401/1993, (Dec. 3, 1993),1.
Pola Chemical, "English Abstract (abridged)", JP App. No. 72491/1980, (May 20, 1980),1.
Horiuchi, Tetsoshirou "English Abstract", JP patent app. No. 155367/1995, (Jun. 20, 1995),1.
Yokoyama, Mitsuhiro "English Abstract", JP Patent App. No. 182783/1997, (Jul. 15, 1997),1.
Nakamura, Shigemi "English Abstract", JP App. No. 276387/1997, (Oct. 28, 1997),1.
Nakayama, Toru "English Abstract", JP App. No. 047253/1999, (Feb. 23, 1999),1.
Maget, Henri "English Abstract", JP App. No. 91380/1983, (Sep. 6, 1983),1.
Nishimura, Haruo "English Abstract", JP App. No. 305870/1988, (Dec. 13, 1988),1.
Hatta, O. "English Abstract (abridged)", JP App. No. 00374/1940, (Jan. 16, 1940),1.
Bushey, Scott "International Search Report", PCT US 99/11775 (corresponding to U.S. Appl. No. 09/028,372, (Aug. 20, 1999),1-2.
Bushey, Scott "Written Opinion of the International Searching Authority", PCT US 99/11775 (corresponding to U.S. Appl. No. 09/028,372, (Jun. 11, 2001),1-4.
Kim, Christopher "Non Final Office Action", U.S. Appl. No. 09/649,563, (Jan. 21, 2003),1-5.
Zheng, Li "Notification of the First Office Action", Chinese Application 200580008690.4 (corresponding to U.S. Appl. No. 10/708,253, (Jul. 3, 2009),1-6.
Unknown Japanese Patent Examiner, "Japanese Office Action (and English translation Summary)", JP App. No. 2006/554202 (Corresponding to U.S. Appl. No. 10/708,253, (Nov. 24, 2010),1-6.
Paik, Sang Y., "International Search Report", PCT US 05/05031 (Corresponding to U.S. Appl. No. 10/708,253, (Oct. 14, 2005),1-4.
Paik, Sang Y., "Written Opinion of the International Searching Authority", PCT US 05/05031 (Corresponding to U.S. Appl. No. 10/708,253, (Oct. 14, 2005),1-4.
Paik, Sang Y., "Non Final Office Action", U.S. Appl. No. 10/708,253, (Jul. 1, 2005),1-7.
Paik, Sang Y., "Final Office Action", U.S. Appl. No. 10/708,253, (Apr. 10, 2006),1-6.
Wood, Jonathan "Non Final Office Action", U.S. Appl. No. 11/923,490, (Feb. 15, 2011),1-15.
Shearer, Daniel "Final Office Action", U.S. Appl. No. 11/923,490, (Aug. 16, 2011),1-10.

* cited by examiner

GAS GENERATION DISPENSER METHOD FOR ON-DEMAND FLUID DELIVERY

CROSS-REFERENCE TO RELATED APPLICATIONS

This is a divisional application of, and claims priority to, U.S. application Ser. No. 11/923,490, filed Oct. 24, 2007 now U.S. Pat. No. 8,113,390, which claimed priority U.S. Provisional Patent Application No. 60/912,463, filed on Apr. 18, 2007. Both of these applications are incorporated by reference herein in their entirety.

BACKGROUND

Dispensing devices such as those that periodically deliver a shot of fragrance into the air are well known. These devices have various control and activation systems including batteries and timers. The mechanisms for delivering the shot may include aerosol type devices that operate over a large range of pressures and piezo pumps.

Conventional gas cells are used for generating gases such as hydrogen from liquids such as water at relatively slow rates in which a volume of gas is generated slowly for periodic use of the gas for motive or other purposes. These gas cells are used in fluid delivery systems that operate automatically. For example, some conventional gas cells in fluid delivery systems continuously generate gas at a slow rate over a long period of time. A build-up in pressure provides a motive force for causing the fluid to exit from a storage chamber. The force is typically automatically applied at predetermined time intervals under the control of a timer and other controls for automatic, periodic delivery of the fluid.

Conventional fluid delivery systems that utilize gas cells are deficient in accounting for changes in environmental or system conditions. For example, as a volume of a gas chamber in a conventional fluid delivery system increases over time, the generation of the gas at a constant rate has a changing effect on the fluid delivery over time due to changes in atmospheric pressure, temperature, or other environmental conditions. Changes in pressure of contained gas due to changes in temperature or elevation typically impact the amount of fluid delivered by conventional gas generation fluid delivery systems such that these systems lack consistency under changing operating conditions.

SUMMARY

In one embodiment, a method of dispensing a fluid includes generating a gas from a liquid. The method also includes directing the gas to an expandable gas chamber to expand a volume of the expandable gas chamber. The method includes reducing a volume of a fluid chamber in response to expansion of the expandable gas chamber to dispense an amount of the fluid from the fluid chamber. The method also includes removing the gas from the expandable gas chamber to collapse the expandable gas chamber. Other embodiments of the method are also described.

In one embodiment, an on-demand fluid dispenser includes an expandable gas chamber. The expandable gas chamber includes a moveable plunger forming a wall of the expandable gas chamber. The moveable plunger also forms a wall of the fluid chamber. An on-demand gas cell is configured to generate the gas on demand and to direct the gas to the expandable gas chamber to expand the expandable gas chamber. In this case, expansion of the expandable gas chamber moves the moveable plunger to reduce a volume of the fluid chamber and to dispense an amount of fluid from the fluid chamber. Additionally, a power source may be connected to the gas cell, and a switch may be coupled to the power source to activate the gas cell. Other embodiments of the on-demand fluid dispenser are also described.

Other aspects and advantages of embodiments of the present invention will become apparent from the following detailed description, taken in conjunction with the accompanying drawings, which are illustrated by way of example of the various principles and embodiments of the invention.

BRIEF DESCRIPTION OF THE DRAWINGS

Throughout the description, similar reference numbers may be used to identify similar elements.

DETAILED DESCRIPTION

In the following description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity. It is to be understood that the features shown and described with regard to the various embodiments may be combined by adding or substituting in any combination without limitation.

Figure 1:
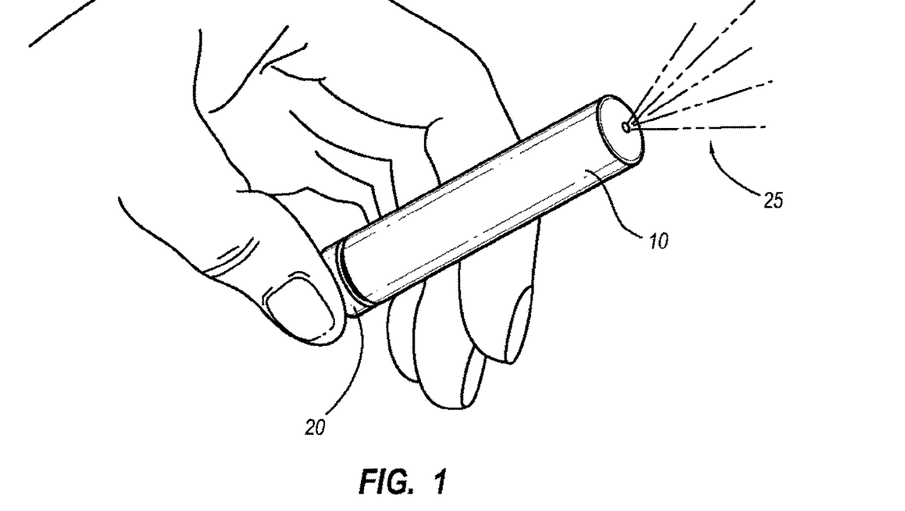
FIG. 1 is an exemplary perspective view of one embodiment of an on-demand fluid dispenser.

FIG. 1 is an exemplary perspective view of one embodiment of an on-demand fluid dispenser 10. It is to be understood that the term "dispenser" is generally used herein to describe embodiments of the on-demand fluid dispensers, and the terms "dispenser" and "on-demand fluid dispenser" are used interchangeably, in many instances. However, some embodiments of the dispenser may be implemented without the on-demand capability while maintaining other characteristics of embodiments described herein.

In the depicted embodiment, a user 15 may grasp the dispenser 10 in any comfortable manner. In FIG. 1, a syringe type of grip is illustrated, although other grips may be used depending on the configuration of the on-demand fluid dispenser 10. A button 20 may be located on a longitudinal end or on a side of the dispenser 10 without loss of meaning or functionality. As shown, the user 15 may press the button 20 to actuate the dispenser 10, and dispense a fluid 25 in accordance with at least some of the details described herein. With a gas generation mechanism and mechanisms for inhibiting the impact of variations in conditions in the environment and in the conditions in the dispenser system itself (referred to collectively herein as operating conditions), a reliable dispenser 10 is made possible.

Figure 2:
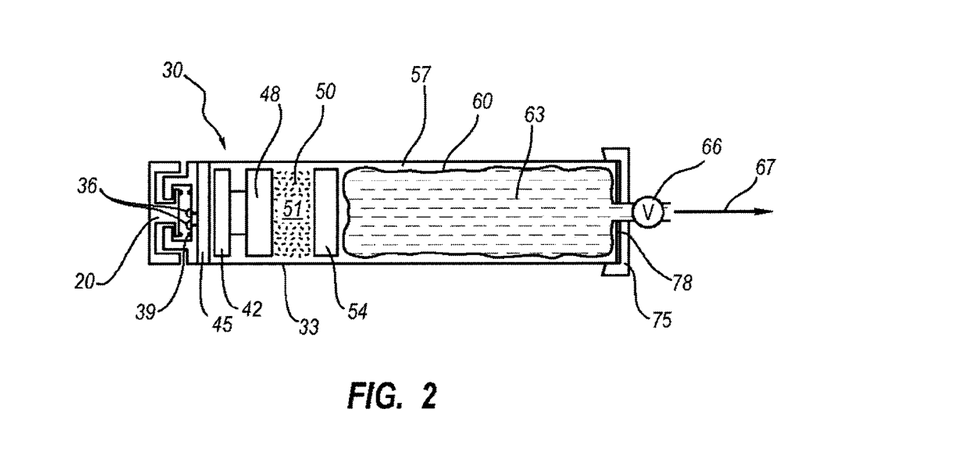
FIG. 2 is a diagrammatic sectional view of another embodiment of an on-demand fluid dispenser.

FIG. 2 is a diagrammatic sectional view of another embodiment of an on-demand fluid dispenser 30. The dispenser 30 may include at least some of the features and characteristics that are presented in the U.S. Provisional Patent Application Ser. No. 60/912,463, filed Apr. 18, 2007, which is incorporated herein by reference. As shown, the dispenser 30 has a housing 33 and a button 20 similar to the button 20 shown in FIG. 1. The button 20 may be urged away from leads 36 by a resilient element 39. The leads 36 are connected to a printed circuit board or other substrate 42, which may support an electronic controller (described below) for the dispenser 30. A battery or other power source 45 is connected to the substrate 42 for providing power to the dispenser 30 through operation of the electronic controller in response to an input signal when the user presses the button 20. In one embodiment, the button 20 and leads 36 form part of a momentary switch that includes a timer so that pressing the switch for any length of time results in a predetermined actuation time. Alternatively, the switch may be a continuous switch that actuates the dispenser 20 continuously for as long as the user 15 actuates the switch.

In one embodiment, the electronic controller delivers power to a gas cell 48, which then produces gas 50 from a liquid (not shown in FIG. 2). The gas 50 is directed into an expandable gas chamber 51. The pressure of the gas 50 causes the expandable gas chamber 51 to expand. As a result, a plunger or first movable wall 54 moves away from the gas cell 48 and toward a front end of the dispenser 30 by the increased pressure of the gas 50 in the expandable gas chamber 51. As the plunger 54 moves away from the gas cell 48 within the dispenser 30, the plunger wall 54 reduces a volume in a fluid chamber 57. In the embodiment illustrated in FIG. 2, a flexible bag 60 containing a fluid 63 to be dispensed is positioned in the fluid chamber 57. Thus, when the plunger 54 moves forward, it compresses the bag 60 and displaces an amount of the fluid 63 out through an outlet 66 in a direction of arrow 67.

Some embodiments of the dispenser 30 include a mechanism for reducing an impact of operating conditions. Some exemplary mechanisms are described herein. Environmental changes such as changes in temperature or elevation may cause changes in operating conditions such as a pressure or a volume of an enclosed chamber. Changes in ambient pressure affect the pressure differential between an interior of a chamber and an exterior of the chamber. Thus, environmental changes have the effect of causing changes in rates of flow of gases and liquids within the dispenser 30. Hence, without a mechanism for reducing the impact of the operating conditions of the dispenser 30, inconsistencies in the amount of dispensed fluid would likely be caused by changes in the environment. The mechanism for reducing the impact of these operating conditions generally controls flow based on pressures such that variations in the operating conditions are inhibited from affecting the amount of the fluid dispensed.

The dispenser 30 may include a removable cover 75 for engaging an end of the bag 60 around the outlet 66. The bag may have a front end plate 78 of a relatively stiff material. The front end plate 78 may act as a stop for engaging the cover 75. In an alternative embodiment, a fluid to be dispensed may be placed directly in the fluid chamber 57 without a flexible bag to contain the fluid. However, the configuration shown in FIG. 2 facilitates replacement of a fluid in the dispenser 30 since the cover 75 can easily be removed, for example, to remove an empty bag and to position a full bag for continued use. These features may be applied singly or together in any combination with other embodiments disclosed herein without limitation.

Figure 3:
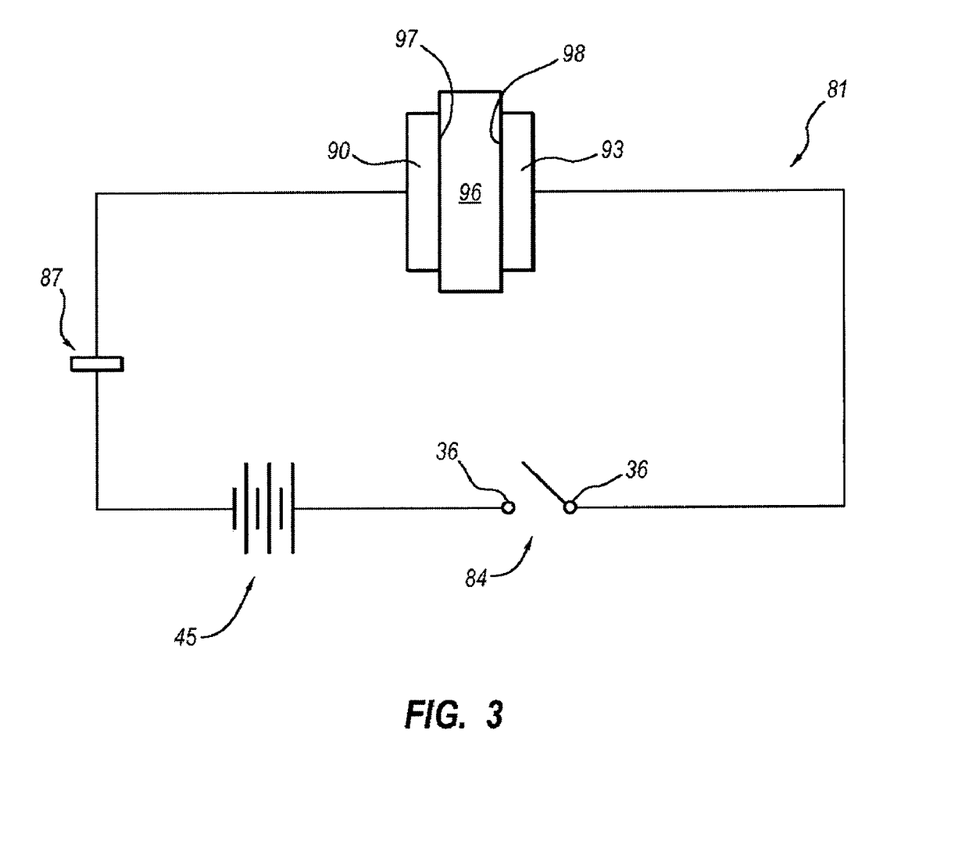
FIG. 3 is a schematic diagram of one embodiment of an electrical circuit that may be incorporated in an embodiment of the on-demand fluid dispenser.

FIG. 3 is a schematic diagram of one embodiment of an electrical circuit 81 that may be incorporated in an embodiment of the on-demand fluid dispenser 30. With reference to FIG. 3, an electronic controller may include a simple circuit 81 having a switch 84 that includes the leads 36, power source 45, and a capacitor 87. When the button 20 is pressed, it closes the circuit 81 and actuates the dispenser 30 in which the circuit 81 is disposed. When activated, an electrical potential is formed across anode 90 and cathode 93. In one embodiment, the anode 90 and cathode 93 engage opposite surfaces of an electrolyte membrane 96. The electrolyte membrane 96 can have liquid such as water therein and is formed of a material that facilitates electrolytic activity. The material may include one or more of a variety of water-absorbent polymeric materials including, but not limited to, NAFION® (a DuPont registered trademark) for example. Other embodiments may use other types of materials, including micro-porous materials, ion-exchange materials, and non-woven polymer materials. The electrodes 90, 93 may be formed of a metallic wool or mesh material including one or more of a variety of materials including, but not limited to, platinum and platinum coated materials. The membrane 96 and/or the electrodes may have large surface areas. As such, a relatively large current is set up across the electrolyte membrane 96. The power source 45 is sufficient to set up a current that will transfer energy to the water molecules at interfaces between the electrodes 90, 93 and the electrolyte membrane 96. The water molecules subsequently separate into hydrogen and oxygen molecules that are in a gas state and form the gas 50, as described with regard to FIG. 1. Other, more specialized, electronic controllers may be substituted for the electronic controller implemented by circuit 81. For example, controllers with timers, sensors, memory, and adjustable settings may be implemented.

Figure 4A:
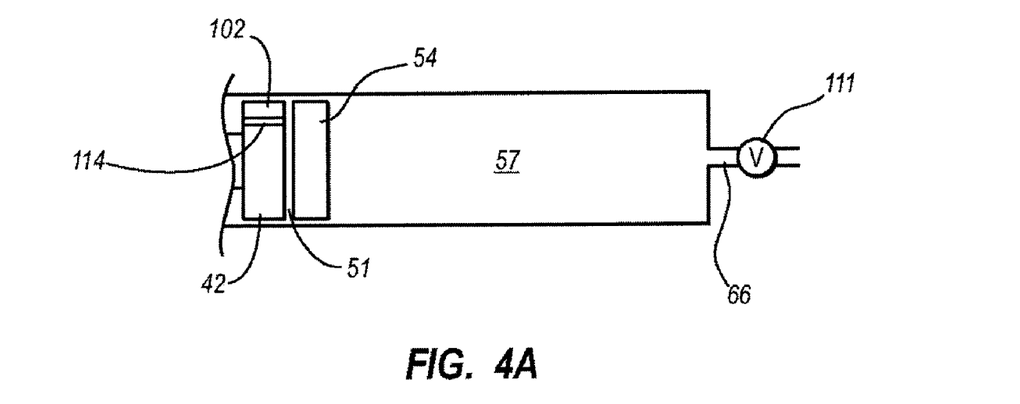
FIGS. 4A-4C are diagrammatic partial sectional views illustrating an embodiment of a process for dispensing fluid from an on-demand fluid dispenser.
Figure 4B:
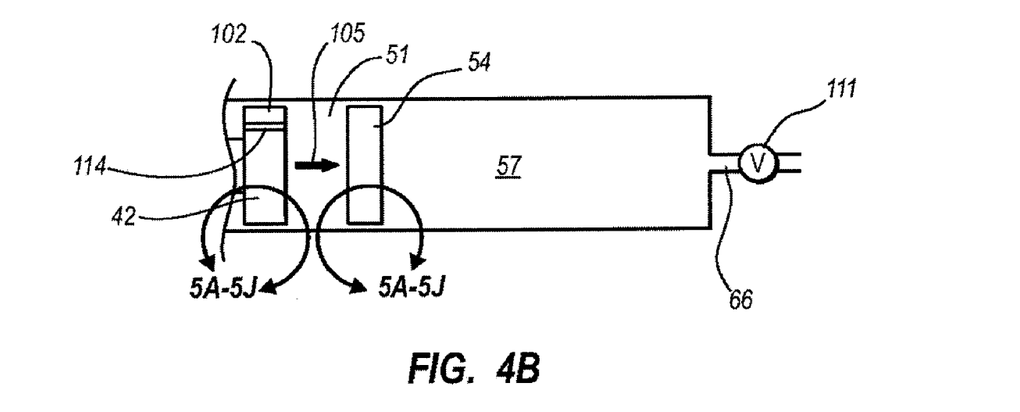
Figure 4C:
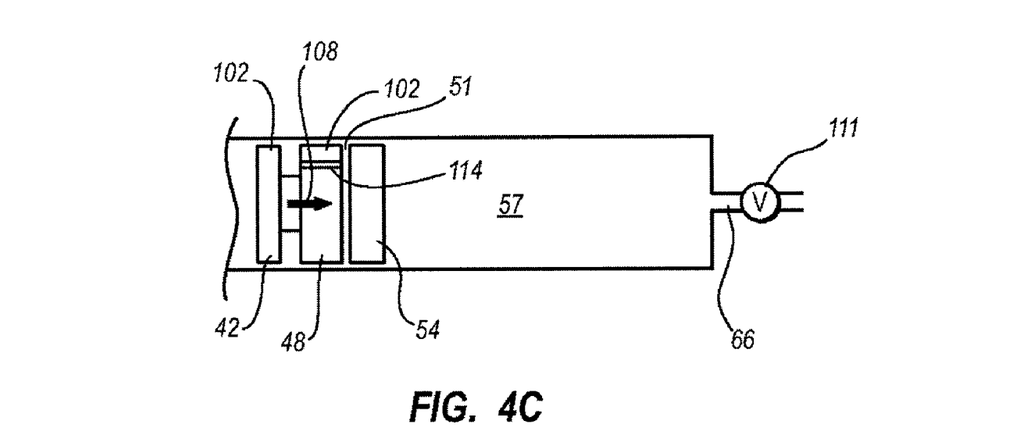

FIGS. 4A-4C are diagrammatic partial sectional views illustrating an embodiment of a process for dispensing fluid from an on-demand fluid dispenser 30. FIGS. 4A-4C show respective operations of the process that is included with at least some of the apparatuses and methods described herein. For example, FIG. 4A shows the first movable wall 54 (i.e., the plunger) near a second movable wall 102. The second movable wall 102 may be termed a follower, and may be formed at least in part by one or both of the gas cell 48 and the substrate 42. Alternatively, another structure may be used to form the follower 102. The movable walls 54, 102 seal the chambers on respective opposite sides of the first movable wall 54. In FIG. 4A, the movable walls 54, 102 are in close proximity to each other with little or no gas between them such that the expandable gas chamber 51 has a relatively small volume. When the dispenser 30 is actuated and the gas 50 is generated by the gas generation cell 48, the pressure between the movable walls 54, 102 increases and applies a force to the walls 54, 102 in opposite directions away from each other. The second movable wall 102 is inhibited from movement away from the first movable wall 54 by any of a variety of mechanisms that are described below. Thus, as shown in FIG. 4B, the first movable wall 54 is caused to move away from the second movable wall 102 in a forward direction 105 toward the fluid chamber 57. When the gas 50 is removed or permitted to escape from the expandable gas chamber 51, the movable walls 54, 102 are either passively urged to move toward each other, for example, by ambient pressure or actively urged together, for example, by a spring or pump. Additionally, the first movable wall 54 is also inhibited from movement toward the second movable wall 102, in a backward direction that is away from the fluid chamber 57, by any of a variety of mechanisms that are described below. Therefore, the second movable wall 102 is drawn toward the first movable wall 54 as indicated by arrow 108 in FIG. 4C. The operations shown in FIGS. 4A-4C may be repeated in an iterative manner so that the movable walls 54, 102 move forward one at a time (to the right as viewed in FIGS. 4A-4C). In this way, the movement of the walls 54, 102 is one-way, or unidirectional, in the forward direction.

As shown in FIGS. 2 and 4A-4C, the dispenser 30 includes an outlet valve 111 in the outlet 66. This valve 111 may be a one-way valve or check valve that allows passage of the fluid 63 out of the fluid chamber 57 and inhibits backflow of the fluid 63 or air into the fluid chamber 57. Since air and other fluid cannot enter the fluid chamber 57 through the outlet 66, a hydrostatic condition is created in which chamber 57 is held at generally constant volume between iterations of movement of the first movable wall 54. Thus, the valve 111 provides a mechanism that inhibits movement of the first movable wall 54 in a backward direction. Similarly, a one-way gas chamber valve 114 may be provided through the second movable wall 102. The one-way gas chamber valve 114 may be a pressure sensitive valve such that when gas is being generated, the pressure sensitive one-way gas chamber valve 114 inhibits passage of the gas out through the second movable wall 102. When the gas has expanded a volume of the expandable gas chamber 51 and the pressure in the expandable gas chamber 51 has dropped below a predetermined threshold, then the one-way gas chamber valve 114 may be automatically opened to allow passage of the produced gas out through the second movable wall 102. As may be appreciated, by providing a sealed enclosure on a backward side of the second movable wall 102, a balance of the pressures on opposite sides of the second movable wall 102 may provide a mechanism that inhibits movement of the second movable wall 102 in a backward direction when the valve 114 is closed. Alternatively, one or more one-way valves in one or more of the first movable wall 54 and side walls of the housing 33 may be substituted for the one-way gas chamber valve 114. For example, the valve 114 may be a manually activated valve or an automatic electrically activated valve, such as a solenoid valve or a piezo valve that are described in greater detail below. Also, the valve 114 may be another kind of valve.

Figure 5A:
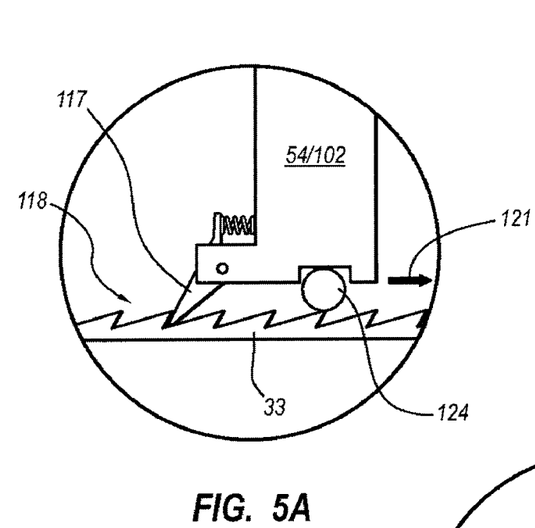
FIGS. 5A-5J are detailed views of the indicated regions in FIG. 4B illustrating examples of alternative mechanisms for inhibiting movement of an element of the on-demand fluid dispenser in one direction relative to another element of the dispenser.
Figure 5B:
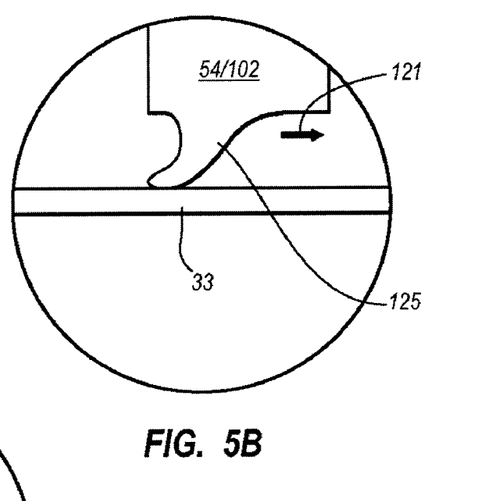
Figure 5C:
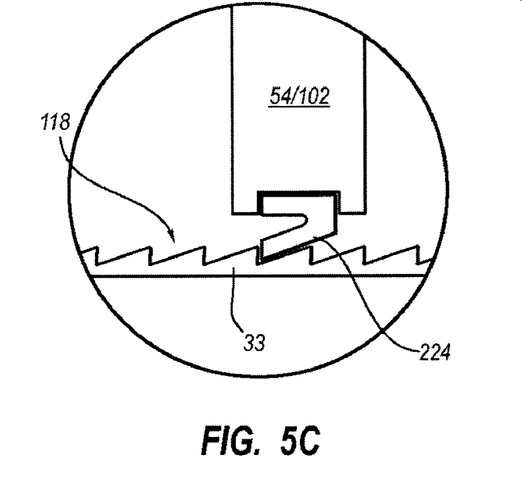
Figure 5D:
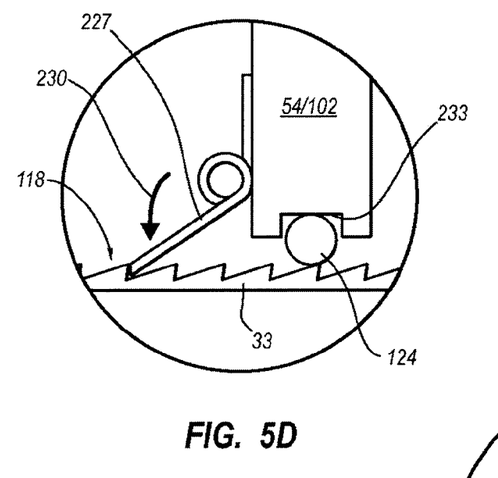

FIGS. 5A-5J are detailed views of the indicated regions in FIG. 4B illustrating examples of alternative mechanisms for inhibiting movement of an element of the on-demand fluid dispenser 30 in one direction relative to another element of the dispenser 30. FIGS. 5A and 5B are detailed diagrammatic sectional views of exemplary structures that may be applied in the indicated regions of FIG. 4B. The exemplary structures may be applied to either or both of the movable walls 54 and 102 and/or corresponding portions of an inner surface of the housing 33. FIG. 5A shows a pawl and ratchet mechanism for inhibiting movement of the first or second movable wall(s) 54, 102 relative to the housing 33. Thus, a pawl 117 may be pivotally supported on the movable wall(s) 54, 102 and a set of teeth 118 may be provided on the inner surface of the housing 33. The angle of the pawl 117 and teeth 118, and their relative spacing, may be such that movement of the movable wall(s) 54, 102 is enabled in a forward direction 121 and inhibited in a backward direction relative to the housing 33. Thus, the mechanism is a mechanism for causing unidirectional progression of the movable wall(s) 54, 102. An o-ring 124 of a resilient material may be additionally provided to form a seal between the movable member(s) 54, 102 and the housing 33. Alternatively, a flange 125 may be provided by itself, as shown in the detailed view of FIG. 5B. The flange 125 may have a height and flexibility that enables the flange 125 to be bent and lie nicely in one direction when engaged by an inner surface of the housing 33. The flange 125 creates a seal and enables movement of the movable member(s) or wall(s) 54, 102 to which it is applied in the forward direction 121. On the other hand, the flange 125 may resist bending in the other direction. Thus, a force in an opposite backward direction will cause a wedging effect of the flange between the movable wall(s) 54, 102 and the inner surface of the housing 33. Thus, a radial force and friction is increased and movement of the movable member(s) 54, 102 in the backward direction is inhibited. As may be appreciated, the o-ring 124 and flange 125 are interchangeable as to their sealing function. The flange 125 may be formed integrally as one piece with the movable wall(s) 54, 102, or may be added onto the movable wall(s) 54, 102.

Figure 5E:
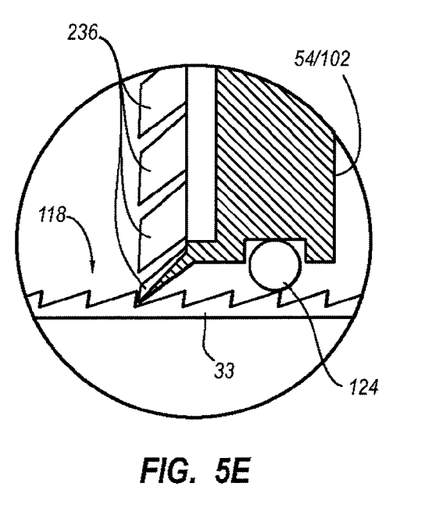
Figure 5F:
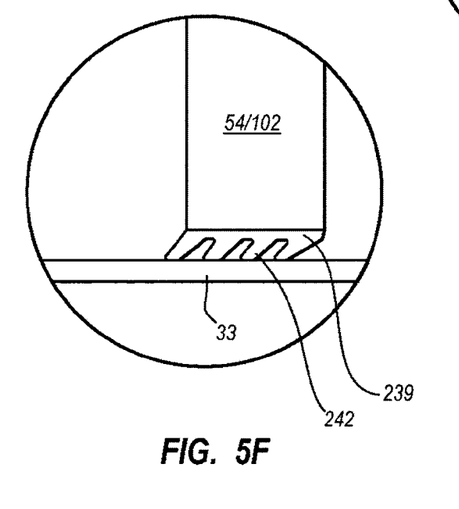

Alternatively, details for the indicated regions of FIG. 4B may be applied in accordance with any of FIGS. 5C-5F to provide other mechanisms for causing unidirectional progression. As shown in the diagrammatic sectional view of FIG. 5C, a shaped o-ring 224 may be configured with a structure to resist movement in the backward direction when engaged with the teeth 118. The material of the shaped o-ring 224 may be elastomeric such that the shaped o-ring 224 forms a seal and resists backward movement at the same time. In another alternative shown in FIG. 5D, torsion springs 227 may be supported on the movable wall 54, 102 and engage the teeth 118 with a force in a direction 230 to inhibit backward movement of the movable wall(s) 54, 102. An o-ring 124 may be held in a groove 233 and form a seal similar to the o-ring 124 of the embodiment shown in FIG. 5A. Further alternatively, flexible fins 236 may be integrally molded with the movable wall(s) 54, 102, as is shown in FIG. 5E. These flexible fins 236 may be angled to engage the teeth 118 to inhibit movement in the backward direction, but to allow forward movement of the fins 236 and the movable wall(s) 54, 102. FIG. 5F shows a further alternative embodiment in which a sleeve 239 of rubber or other flexible material may be supported on an outer surface of the movable wall(s) 54, 102. The sleeve 239 may have one or more flanges 242 that function to seal and inhibit movement of the movable wall(s) 54, 102 in the backward direction while allowing movement of the wall(s) 54, 102 in the forward direction. The sleeve 239 may be glued or vulcanized onto the outer surface of the movable wall(s) 54, 102.

Figure 5G:
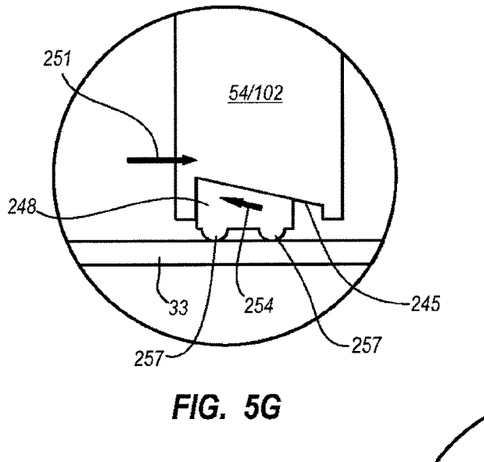
Figure 5H:
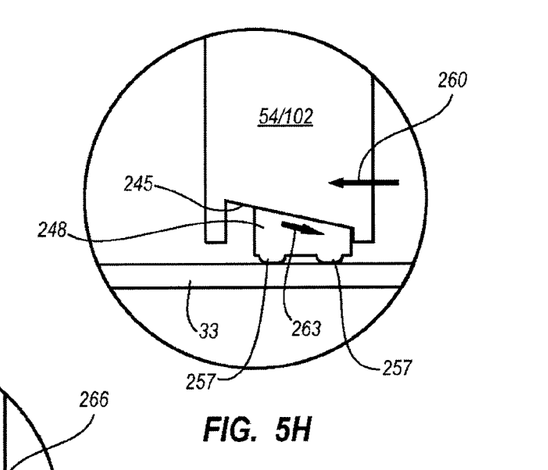

In another embodiment, FIGS. 5G-5H show diagrammatic sectional views of mechanisms for causing unidirectional progression of the movable wall(s) 54, 102 that may be incorporated in place of any of the embodiments shown in FIGS. 5A-5F, as applied to the indicated regions of FIG. 4B. Like the previously described embodiments, the mechanisms of FIGS. 5G-5J are configured to cause sealing of the movable walls 54, 102 about their edges relative to the inner surface of the housing 33. For example, in FIG. 5G, the movable wall(s) 54, 102 have a tapered groove 245 in an outer edge. A flexible wedge ring 248 is received in the groove 245. As a force is applied to the movable wall(s) 54, 102 in a direction of arrow 251, the movable wall(s) 54, 102 are moved so that a deeper end of the tapered groove 245 receives the wedge ring 248. Alternatively stated, the wedge ring 248 travels relative to the movable wall(s) 54, 102 along a bottom of the tapered groove 245 in a direction of arrow 254. Since the diameter of the tapered groove 245 decreases in a direction of the arrow 254, the wedge ring 248 is permitted to contract slightly in a radially inward direction such that flanges or ribs 257 are compressed only slightly to maintain a seal between the movable wall(s) 54, 102 and the housing 33. With the wedge ring 248 in the position shown in FIG. 5G, the movable wall is permitted to move in a forward direction corresponding to the direction of arrow 251 while maintaining the seal. Movement of the movable wall(s) 54, 102 in the direction of arrow 251 may occur when, for example, a generated gas expands the expandable gas chamber 51 and pushes movable wall 54 or when a spring urges movable wall 102 toward the movable wall 54 to contract the expandable gas chamber 51. However, when a force acts in a backward direction as indicated by arrow 260 in FIG. 5H, the movable wall(s) 54, 102 move back slightly such that a shallow end of the tapered groove 245 causes the wedge ring 248 to stretch radially outward and more firmly engage the inner surface of the housing 33. Alternatively stated, the wedge ring 248 travels relative to the movable wall 54, 102 in a direction of the arrow 263. In this position (shown in FIG. 5H) the flanges or ribs 257 are deformed and the contact between the ribs 257 and the inner surface of the housing 33 is increased. Thus, friction between the wedge ring 248 and the housing 33 is increased and movement of the wedge ring 248 and the movable wall(s) 54, 102 in a backward direction is inhibited. As may be appreciated, repeated iterations of forces in the forward and backward directions on the movable wall(s) 54, 102 will cause generally incremental forward movement of the movable walls 54, 102 while inhibiting all but slight movement in the backward direction.

Figure 5I:
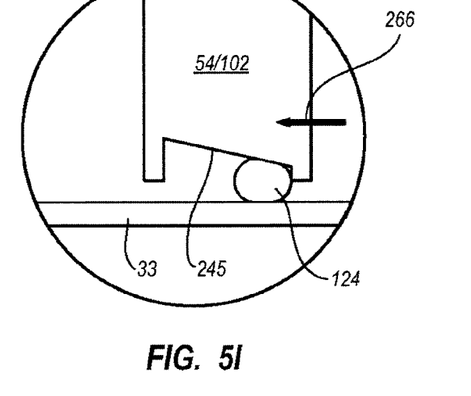
Figure 5J:
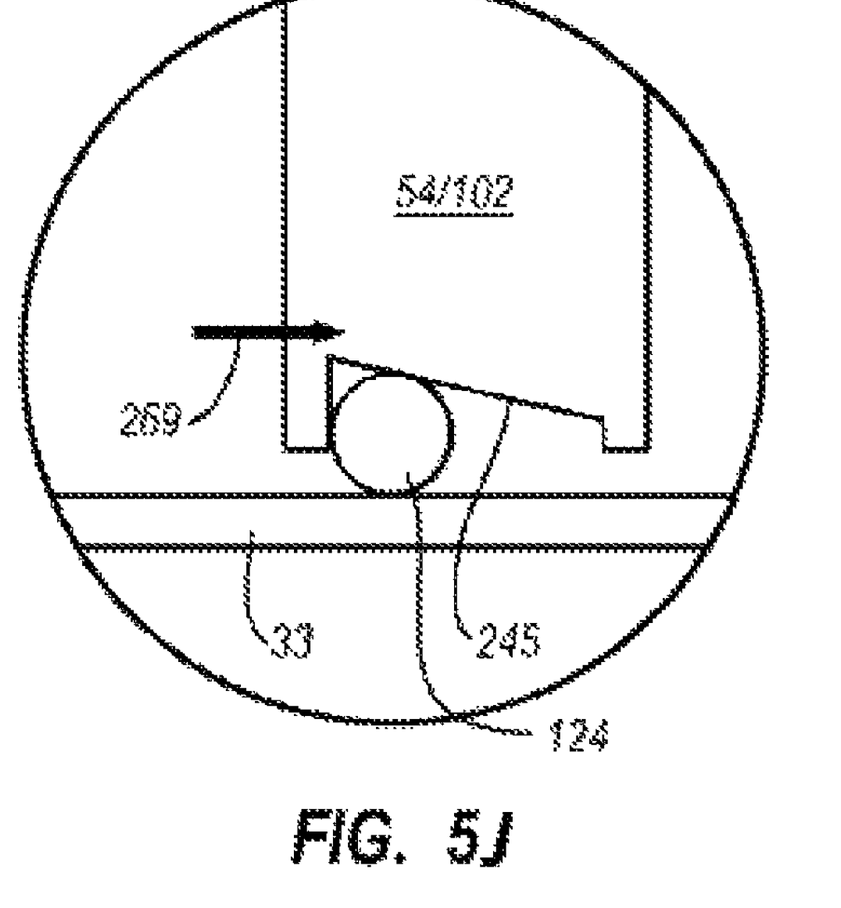

FIGS. 5I and 5J are diagrammatic section views of details of a mechanism that functions similarly to those shown and described with regard to FIGS. 5G and 5H. These details may be alternatively applied to the indicated regions of FIG. 4B. A primary difference in the mechanism of FIGS. 5I and 5H is that it has an o-ring 124 instead of the wedge ring 248 shown in FIGS. 5G and 5H. Otherwise, the structure and function of the mechanism for causing unidirectional movement of FIGS. 5I and 5J is substantially similar to that of FIGS. 5G and 5H. However, FIG. 5I shows a force in the backward direction 266, which would initially be applied to the follower or second movable wall 102 during expansion of the gas in the expandable gas chamber 51. In this position, the tapered groove 245 has been moved slightly backward until the o-ring 124 is stretched and pressed such that it grips the inner surface of the housing 33 sufficiently to stop or lock the o-ring 124 and movable wall 102 against further backward movement. The same locking occurs when applied to the first movable wall 54 during a contraction of the expandable gas chamber 51, for example. As shown in FIG. 5J, in a subsequent operation when the movable wall(s) 54, 102 have a force applied in the forward direction 269, a deep end of the tapered groove 245 is moved over the o-ring 124, permitting the o-ring 124 to contract and reduce its frictional engagement with the inner surface of the housing 33. In the position shown in FIG. 5J, the o-ring 124 forms a seal between the movable wall(s) 54, 102 and the housing 33 while permitting sliding movement of the o-ring 124 and movable wall(s) 54, 102 in the forward direction.

Figure 6A:
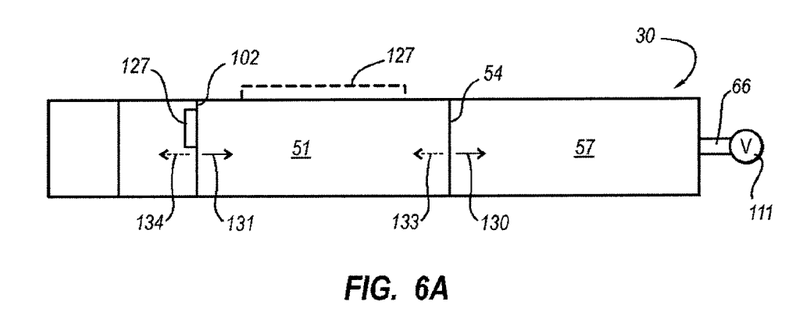
FIGS. 6A-6C are diagrammatic sectional views of a variety of combinations of elements and methods that may be implemented in embodiments of the on-demand fluid dispenser.
Figure 6B:
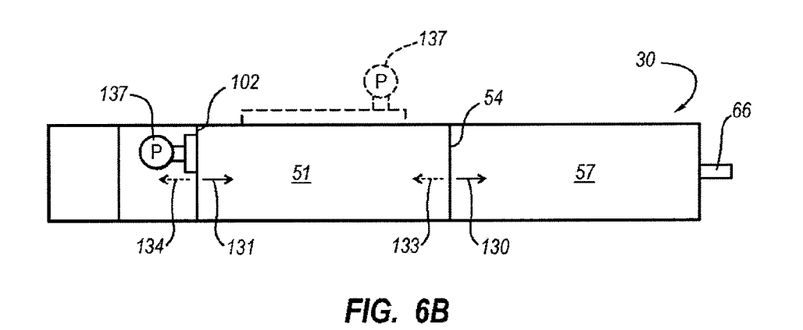
Figure 6C:
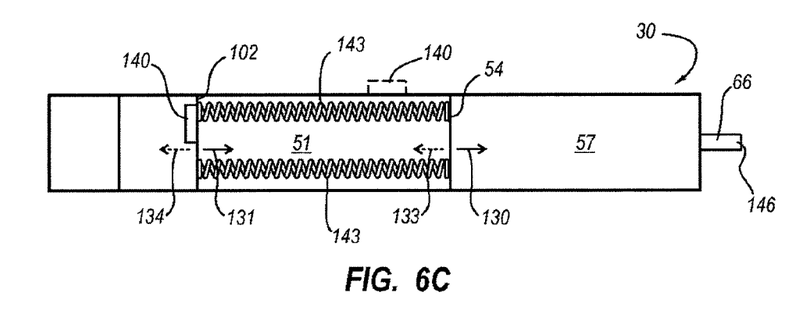

FIGS. 6A-6C are diagrammatic sectional views of a variety of combinations of elements and methods that may be implemented in embodiments of the on-demand fluid dispenser 30. The dispensers 30 of FIGS. 6A-6C show a variety of elements that may be applied to any embodiment of the dispenser 30 without limitation. For example, FIG. 6A shows a permeable region 127 which may be integral with or added onto one or more of the movable walls 54, 102 and a sidewall of the dispenser 30. It is to be understood that the housing 33 itself could be formed of the permeable material, or a long strip of permeable material forming a permeable region 127 shown in dashed lines in FIG. 6A may be provided along a length of the housing 33. The permeable region 127 may include a material such as polypropylene or some other material that is permeable to the gas that is being generated, for example oxygen or hydrogen gas, yet relatively impermeable to the source liquid. However, the permeability is such that pressure builds up quickly during generation of the gas and then slowly dissipates as the gas molecules escape through the permeable material. After expansion during gas generation, the expandable gas chamber 51 will collapse as the pressure drops and substantially equalizes to the ambient air pressure outside the housing 33. Collapse of the expandable gas chamber 51 may be speeded by a pump and/or spring. The outlet 66 may have the outlet valve 111 described above. The walls may have additional valves and/or mechanisms for inhibiting movement of the movable walls 54, 102 in a backward direction as described above. As shown in FIGS. 6A-6C, the walls 54, 102 will move one after another in a forward direction to the right as indicated by the arrows 130, 131. The dashed arrows 133, 134 indicate that in accordance with some embodiments the movable walls 54, 102 may be moved in a backward direction when the dispenser 30 is being reset and refilled.

FIG. 6B shows the dispenser 30 with a pump 137 for actively removing the gas after it has been generated and expanded the expandable gas chamber 51. The pump 137 may be incorporated together with a valve or a permeable region on any of the walls forming the expandable gas chamber 51. The pump 137 may be a manually or electrically powered pump. In any case, the pump 137 speeds removal of the gas and contributes to the frequency with which the on-demand activation of the dispenser 30 may be effectuated. In the embodiment of FIG. 6B, no valve is shown on the outlet 66. A valve 111 may not be needed when the fluid being dispensed from the fluid chamber 57 is highly viscous, for example. On the other hand, a valve 111 may be included in the outlet 66 without limitation.

FIG. 6C shows the dispenser 30 with a solenoid valve or other gas release mechanism 140 on the second movable wall 102 for releasing gas from an interior to an exterior of the expandable gas chamber 51. The gas release mechanism 140 could alternatively be located on a sidewall of the housing 33 in a portion of the housing corresponding to the expandable gas chamber 51 or any of the walls forming the expandable gas chamber 51. The gas release mechanism 140 may include a valve such as valve 114 shown in FIGS. 4A-4C. The gas release mechanism 140 may be operated to release the gas after it has been generated and after it has expanded the expandable gas chamber 51. The gas release mechanism 140 may alternatively include an ionic transport pump that is an electrochemical solid state ionic transport gas pump that has no moving parts. Further alternatively, the gas release mechanism may include an electrochemical liquid generator to convert the gas in the expandable gas chamber 51 back into a liquid in response to the operation of dispensing the amount of fluid from the fluid chamber 57. The converted liquid may be stored in a liquid storage reserve (not shown) for regeneration of a gas from the converted liquid. The on-demand fluid dispenser 30 may thus convert the gas back into a liquid for reuse in a gas cell generator to generate additional gas in a repeating cycle by utilizing an electrochemical reaction of chemical components within the gas. In any case, the methods may include dispensing in response to a user input for on-demand dispensing.

As shown in FIG. 6C, instead of a pump, one or more springs or other resilient biasing element 143 may be connected to the movable walls 54, 102 to draw them together. It is to be understood that such biasing elements 143 may be used in conjunction with a permeable region or a valve in any of the walls forming the expandable gas chamber 51. A proximity switch (not shown) may be incorporated in the movable walls such that a valve may be automatically opened when a predetermined amount of gas has been generated and has expanded the expandable gas chamber 51 to a predetermined volume at which the walls are sufficiently separated to activate the proximity switch. The resilient biasing element(s) 143 may be replaced by magnetic elements in the form of permanent magnets or electromagnetic coils mounted in or on the movable walls 54, 102. The magnetic elements may exert attractive forces on each other such that the movable walls are drawn together. In some embodiments, the resilient biasing element(s) 143 or magnetic elements may be applied in a manner that they push the second movable wall 102 instead of pulling it. The magnetic and/or electromagnetic forces can be actively or passively applied to collapse the expandable gas chamber. As depicted in FIG. 6C, the outlet 66 may alternatively include a duckbill valve 146.

Figure 7:
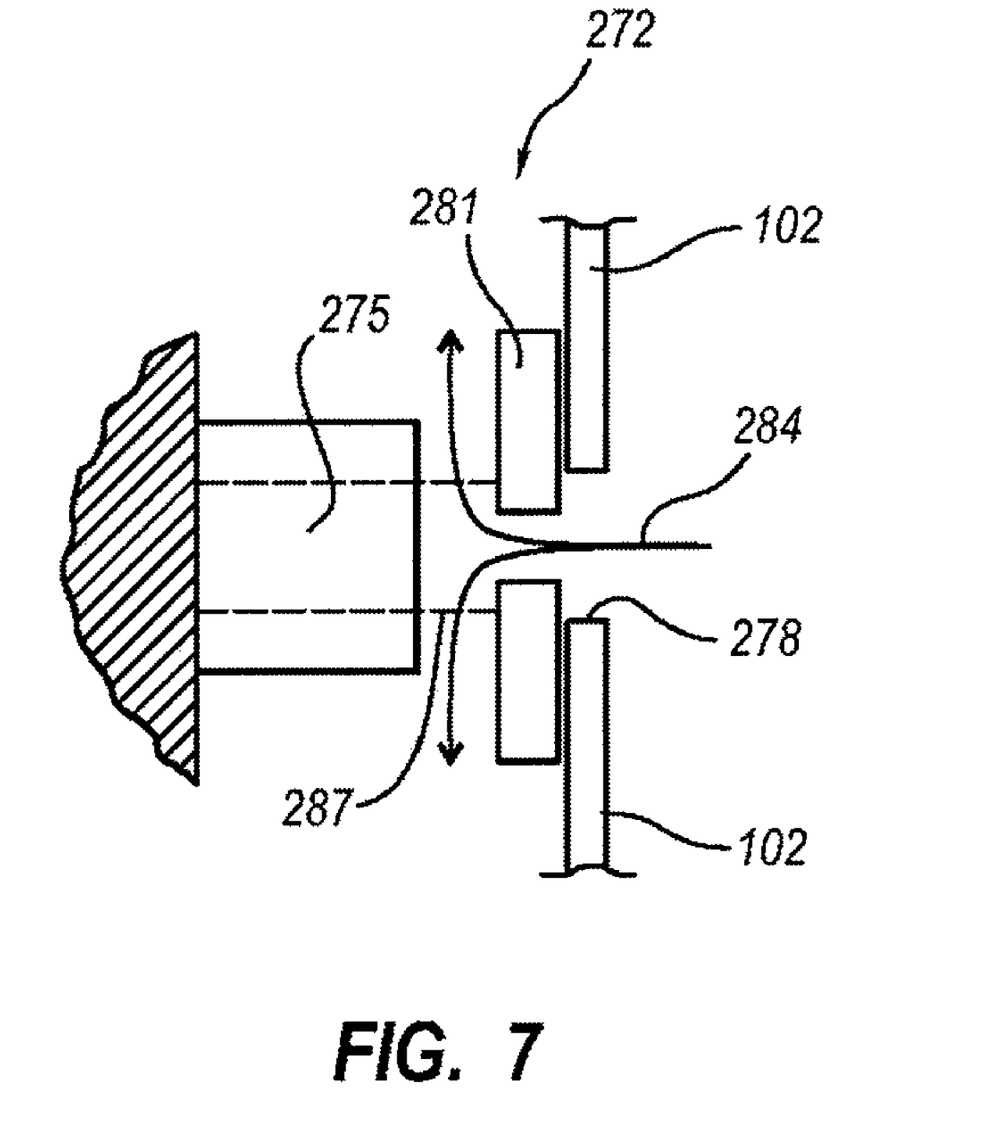
FIG. 7 is a diagrammatic sectional view of a piezo valve that may be incorporated in embodiments of the on-demand fluid dispenser.

FIG. 7 is a diagrammatic sectional view of a piezo valve 272 that may be incorporated in embodiments of the on-demand fluid dispenser 30. The piezo valve 272 may be provided in addition to any of the gas release mechanisms 127, 137, 140 of FIGS. 6A-6C. These gas release mechanisms generally include some kind of valve or opening located in a wall for releasing a gas through the wall. For example, the valve 114 shown in FIGS. 4A-4C extends through a wall of the gas cell 48, which may at least form part of the second movable wall 102. Alternatively, the valve 114 may form an opening through the substrate 42, which may at least form part of the second movable wall 102. The valve 114 may take the form of a solenoid valve or the piezo valve 272 shown in FIG. 7. The piezo valve 272 may include a piezo element 275 electrically connected to a power source such as power source 45 by an electronic controller or switch. An opening 278 through the second movable wall 102 (or another wall) may have a valve seat 281 connected in surrounding sealing relation to the opening 278. Thus, when the piezo element 275 is energized, it is shortened as shown in solid lines. The energized shortened condition allows passage of gas as indicated by arrows 284. When it is de-energized, the piezo element 275 lengthens and engages the valve seat 281, as shown by dashed lines 287 in FIG. 7. Thus, the piezo valve 272 may be opened and closed by energizing and de-energizing the piezo element.

In one aspect, embodiments of the on-line fluid dispenser or method of dispensing a fluid provide a balance between collapsing the expandable gas chamber while substantially maintaining the volume of the fluid chamber. That is, the mechanism for collapsing the expandable gas chamber does not also cause the fluid chamber to collapse. Rather, after the expandable gas chamber has been collapsed, generation of gas causes the fluid chamber to at least partially compress.

In another aspect of embodiments of the method of dispensing a liquid, generating gas includes generating the gas at a gas generation rate that is higher than a gas removal rate during the operation of removing the gas from the expandable gas chamber. This aspect enables the dispensers and methods in accordance with certain embodiments to be "on-demand."

It is to be understood that this on-demand feature may be combined with a continuous gas generation mechanism that continuously generates a reserve of the gas. In this embodiment, the rapid generation of gas acts in an additive manner to provide a bolus effect of delivering fluid automatically and periodically by the continuous gas generation mechanism, and delivering fluid on-demand as a user activates the dispenser.

In the on-demand aspect of the embodiments described herein, the operation of generating may include generating a volume of gas in a first range from about one to one hundred microliters for a single delivery of fluid from the fluid chamber for a single delivery of fluid from the fluid chamber. Alternatively, generating the gas may include generating a volume of gas in a range from approximately twenty to approximately fifty microliters for the single delivery, which may take place over a period of approximately three seconds. A volume in these ranges may be generated in a range from one to six seconds. The period of generation could be any number within this range, such as five seconds. Even with a very small easily portable dispenser, the method may include dispensing the fluid between about one hundred and fifty thousand times. Alternatively, the method may include dispensing fluid between about four thousand and fifteen thousand times from the dispenser 30. In other words, the dispenser 30 may dispense fluid a substantial number of times potentially using a single liquid source and/or fluid source. In this regard, dispensing may include generating the gas to repeatedly dispense the amount of the fluid at substantially regular, discrete intervals such as by a momentary switch. Alternatively, the method may include generating gas continuously such as by depressing a continuous switch. In any case, generating the gas to dispense the fluid on demand may be in response to a user input.

The on-demand dispensing apparatus and method provides long life over many iterations and/or plural refills. In one aspect, the apparatus and method enables easy portability through compactness. In another aspect, the apparatus and method is capable of consistently delivering a determined amount of a fluid in a variety of environmental or system conditions.

The on-demand dispensing apparatus and method in accordance with the disclosed embodiments may be utilized in a wide variety of applications and environments. The fluids that can be dispensed by the dispensing apparatus and method are limitless. For example, the dispensers disclosed herein may receive fragrances or other fluids in their fluid chambers for dispensing. By way of further example, the dispensers may be used to dispense "beneficial agents" such as medicaments and pharmaceutical agents.

The dispenser may be a unitary device supported in a housing that includes the expandable gas chamber, the fluid chamber, the power source, and the switch. The housing may be cylindrical, and have one or more resilient member or element configured to move the second moveable wall in a single direction along a substantially linear path to collapse the expandable gas chamber in response to the amount of fluid being dispensed from the fluid chamber. The movable walls may be in the form of movable plungers each having a flexible seal coupled to the moveable plunger to seal the fluid chamber and the expandable gas chamber. The first movable plunger may form a common wall between the expandable gas chamber and the fluid chamber. Hence, a first movable plunger may be formed of a first movable structure or wall, and a second movable plunger may be formed of a second moveable structure forming a second wall of the expandable gas chamber. Removal of the gas from the expandable gas chamber moves the second moveable structure to collapse the expandable gas chamber. Other embodiments may be implemented with fewer or more structural components or functional parts.

The electronic controller may be configured to operate a gas release valve, which may take the form of the solenoid valve or piezo valve described above. Thus, the electronic controller can release gas from the expandable gas chamber in response to the amount of fluid being dispensed from the fluid chamber either automatically or under user control.

Reference throughout this specification to "one embodiment," "an embodiment," or similar language means that the described feature, operation, structure, or characteristic may be implemented in at least one embodiment. Thus, the phrases "in one embodiment," "in an embodiment," and similar phrases throughout this specification may, but do not necessarily, refer to the same embodiment.

Furthermore, the described features, operations, structures, or characteristics of the described embodiments may be combined in any suitable manner. Hence, the numerous details provided here, such as examples of electrode configurations, housing configurations, chamber configurations, and so forth, provide an understanding of several embodiments of methods of dispensing a fluid and on-demand fluid dispensers. However, some embodiments may be practiced without one or more of the specific details, or with other features operations, components, materials, and so forth. In other instances, well-known structures, materials, or operations are not shown or described in at least some of the figures for the sake of brevity and clarity.

Although specific embodiments have been described and illustrated, the invention is not to be limited to the specific forms or arrangements of parts so described and illustrated. The scope of the invention is to be defined by the claims appended hereto and their equivalents.

What is claimed is:

1. A method of dispensing a fluid comprising:
generating a gas from a liquid;
directing the gas to an expandable gas chamber to expand the expandable gas chamber, wherein expanding the expandable gas chamber comprises translating a first movable wall of the expandable gas chamber along a linear path, the first movable wall comprising a first mechanism to inhibit movement of the first movable wall in a backward direction along the linear path;
reducing a volume of a fluid chamber in response to expansion of the expandable gas chamber to dispense an amount of the fluid from the fluid chamber; and
removing the gas from the expandable gas chamber to collapse the expandable gas chamber, wherein collapsing the expandable gas chamber comprises drawing a second movable wall of the expandable gas chamber along the linear path toward the first movable wall, the second movable wall comprising a second mechanism to inhibit movement of the second movable wall in the backward direction along the linear path wherein removing the gas comprises converting the gas back into the liquid and storing the liquid in a liquid storage reserve.

2. The method of claim 1, further comprising collapsing the expandable gas chamber while substantially maintaining the volume of the fluid chamber.

3. The method of claim 1, wherein generating the gas comprises generating the gas at a gas generation rate that is higher than a gas removal rate associated with removing the gas from the expandable gas chamber.

4. The method of claim 1, wherein converting the gas back into the liquid comprises inducing an electrochemical reaction of chemical components within the gas.

5. The method of claim 1, wherein generating the gas comprises generating a volume of gas in a first range from about one to one hundred microliters for a single delivery of fluid from the fluid chamber.

6. The method of claim 5, further comprising generating the volume of gas in less than approximately five seconds.

7. The method of claim 1, further comprising generating the gas to dispense the fluid on demand in response to a user input.

\* \* \* \* \*